US006387711B1

(12) United States Patent
Sundaram et al.

(10) Patent No.: US 6,387,711 B1
(45) Date of Patent: May 14, 2002

(54) LIQUID INTACT PARATHYROID HORMONE (PTH) STANDARDS

(75) Inventors: Lata Sundaram, Laguna Niguel; Ann Hoang, Lake Forest; Stan Shimizu, Trabuco Canyon, all of CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

(21) Appl. No.: 09/637,649

(22) Filed: Aug. 11, 2000

(51) Int. Cl.$^7$ .................... G01N 33/546; G01N 33/533; G01N 33/534

(52) U.S. Cl. ................ 436/534; 436/526; 436/804; 436/817

(58) Field of Search ................ 424/562; 435/7.9, 435/7.92, 7.94, 8, 967, 7.1; 436/501, 524, 538, 546, 817, 526, 804, 534; 422/56

(56) References Cited

U.S. PATENT DOCUMENTS

| | | | | |
|---|---|---|---|---|
| 3,886,132 A | * | 5/1975 | Brewer et al. ........... 260/112.5 |
| 4,508,828 A | * | 4/1985 | Lindall et al. .............. 436/500 |
| 4,663,295 A | * | 5/1987 | Vail et al. .................... 436/18 |
| 4,788,138 A | * | 11/1988 | Tung et al. .................... 435/7 |
| 4,868,154 A | * | 9/1989 | Gilbard et al. ................ 514/13 |
| 5,124,318 A | * | 6/1992 | Gatti et al. ................... 514/34 |
| 5,149,626 A | * | 9/1992 | Fleming ...................... 435/7.9 |
| 5,196,349 A | * | 3/1993 | Piran et al. .................. 436/500 |
| 5,208,041 A | * | 5/1993 | Sindrey ...................... 424/562 |
| 5,496,801 A | * | 3/1996 | Hothuis et al. ................ 514/12 |
| 5,834,226 A | * | 11/1998 | Maupin ....................... 435/15 |
| 5,847,086 A | * | 12/1998 | Farb et al. ................... 530/383 |
| 5,981,485 A | * | 11/1999 | O'conner et al. ............. 514/12 |

* cited by examiner

Primary Examiner—Mary E. Ceperley
(74) Attorney, Agent, or Firm—Stout, Uxa, Buyan & Mullins, LLP; Donald E. Stout

(57) ABSTRACT

A solution of a non-reconstituted hormone and a preservative having a useful shelf life of at least six months, and, in some circumstances, at least a year. A series of solution of varying levels of the non-reconstituted hormone may be in a test kit and used in a process to determine the level of the hormone in a patient sample. In an aspect of the invention, the hormone is parathyroid hormone. The preservatives may be polyvinyl alcohol, a dissolved EDTA salt, or dissolved sodium molybdate. The hormone may be in an aqueous or a buffered matrix containing very little protein and substantial amounts of TX100 to reduce non-specific binding. The solution is incubated with a solid phase coated with an anti-hormone antibody and a labeled hormone antibody. The solid phase is read using a suitable device for measuring the labeled hormone antibody. An example of a labeled hormone antibody is an acridinium labeled hormone antibody that is read using a light reading device.

9 Claims, 1 Drawing Sheet

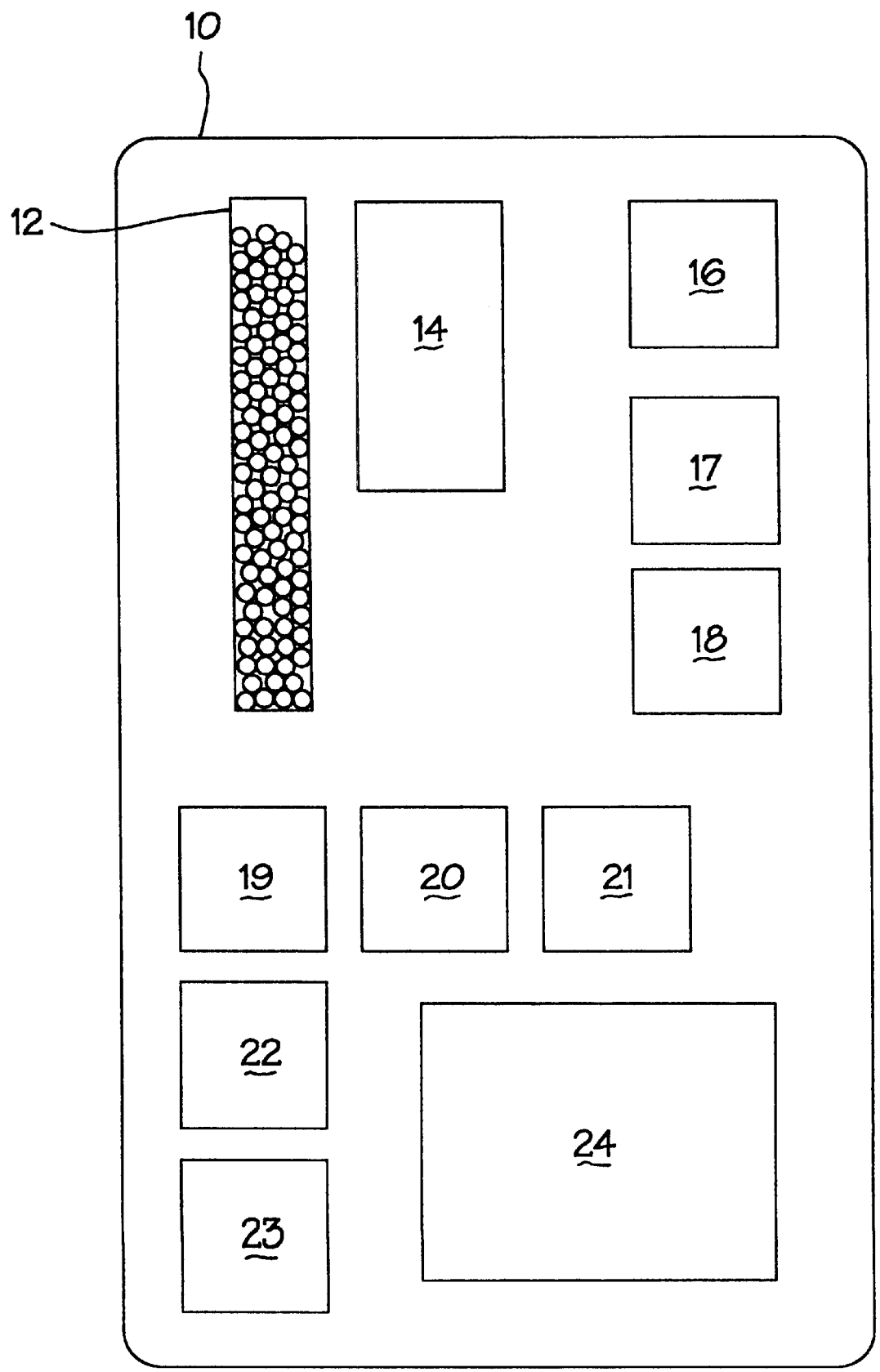

LIQUID INTACT PARATHYROID HORMONE (PTH) STANDARDS

BACKGROUND OF THE INVENTION

1. Field of the Invention

This invention relates to the amino acid peptide hormone standards and, more specifically, to the use of parathyroid hormone (PTE), an 84 amino acid peptide hormone for diagnosing calcium metabolism disorders.

2. Description of the Related Art

Intact parathyroid hormone (PTH) is an 84 amino acid peptide hormone produced by the parathyroid gland. Since PTH maintains calcium homeostasis, its measurement is an important aid in the diagnosis of calcium metabolism disorders. Decreased serum calcium levels result in increased PTH secretion, causing increased absorption of dietary calcium, decreased renal clearance, and mobilization of skeletal calcium stores. In conjunction with calcium levels, PTH quantization can help distinguish between normal patients and patients with hyperparathyroidism, hypoparathyroidism or hypercalcemia of malignancy.

A diagnostic kit usually employs an immunometric method to measure an unknown sample read off a curve generated using a series of standards. For kits employing hormones as the standards, the hormones are prepared in a serum or buffered serum matrix.

Typically, PTH standards in a kit are constituted from freeze-dried PTH to achieve desired stability. Testing has shown that PTH spiked at 50, 500, and 1500 pg/mL into human serum and buffered bovine serum matrix has a recovery of approximately 70% and 80%, respectively, after a three day, 37° C. stability test. The recoveries for acceptable standards are within 100+/−10%.

The prior art recognizes the limitations of using freeze-dried biological materials, such as PTH, for standards. The freeze-drying PTH results in a loss of activity. Errors in preparation of the standard occur due to reconstituting the lyophilized PTH in terms of volume and mixing to homogeneity.

Lyophilizing the material used as standards creates additional problems. Lyophilization is a capital and energy intensive process, making it costly. Further, the batch size of the lyophilizer also limits the quantity of the standard produced. Additionally, a low quality batch of freeze-dried product results in a large scrap cost.

Stability of standards may also be achieved through the use of additives that preserve biological material. For example, additives provide a protective function against the adverse effects of adsorption onto glass. Additives may preferentially bind metal ions or other functional groups, or displace water to preserve activity.

Unfortunately, the range of preservation additives is very wide and includes substance as diverse as substrates, specific ligand, glycerol, sugars, polyethylene glycols, detergents, and chelators. The wide range of preservation additives results in intensive research to determine appropriate combinations and quantities.

The prior art recognizes a need for a liquid PTH standard that has a long—at least nine months —shelf life that does not require freeze-dried PTH.

SUMMARY OF THE INVENTION

A solution comprising a non-reconstituted hormone and a preservative that has a useful shelf life of at least nine months at 4 degrees C. has been discovered. In aspects of the invention, the solution has a useful shelf life of at least six months at 4 degrees C.

In further aspects of the invention, the solution comprises a non-specific binding reducer. The solution may be a buffered aqueous solution with a pH greater than 7.0. The solution may be buffered with phosphate.

In a further aspect of the invention, the hormone is parathyroid hormone, but other aspects of the invention may have other hormones.

In a further aspect of the invention, the preservative is polyvinyl alcohol, dissolved EDTA di-sodium salt, or dissolved sodium molybdate. In a still further aspect of the invention, the preservative, expressed as a percentage of the solution, comprises less than 1% polyvinyl alcohol, less than 0.5% dissolved EDTA di-sodium salt, and less than 1% dissolved molybdate. In an even further aspect of the invention, the preservative, expressed as a percentage of the solution, comprises approximately 0.5% polyvinyl alcohol, approximately 0.17% dissolved EDTA di-sodium salt, and approximately 0.7% dissolved molybdate.

In an aspect of the invention, a diagnostic test kit comprises a plurality of standards of known percentages of a non-reconstituted hormone in a solution comprising a preservative, as described above. The kit also comprises a solid phase coated with anti-hormone antibody and a solution of labeled antibody of the hormone.

In a further aspect of the invention, the labeled antibody has acridinium ester label. Other aspects may have other suitable labels. The hormone may be parathyroid hormone or any other suitable hormone.

In an aspect of the invention, a process for assaying a sample for a hormone comprises the step of providing a plurality of standards having varying levels of a non-reconstituted version of the hormone and a preservative in a matrix wherein the standards have a useful shelf life of at least nine months at 4 degrees C. In other aspects of the invention, the standards may be any suitable variation of the solutions described above. In a next step of aspect of the invention, quantities of the plurality of standards and the sample are delivered to containers, respectively. Then, additional quantities of an labeled antibody of the hormone are delivered to the containers, respectively, whereby each container comprises a solution. A solid phase coated with an additional antibody of the hormone is placed into the solution in each container. The solutions are incubated and the solid phase is washed and measured for the labeled antibody of the hormone on the solid phase.

BRIEF DESCRIPTION OF THE DRAWINGS

The FIGURE is a schematic representation of a parathyroid hormone diagnostic kit.

DESCRIPTION OF THE PREFERRED EMBODIMENTS

Referring now in more detail to the FIGURE, a diagnostic test kit 10 for performing an intact parathyroid hormone (PTH) assay comprises PTH antibody coated beads 12, acridinium ester labeled PTH antibody solution 14, six standards 16–21, two controls 22–23, and a saline wash concentrate 24, all of which are stored in appropriate containers. Other kits may have other materials, including more or fewer standards and controls. In the preferred embodiment of the invention, the kit is used in conjunction with a luminometer, but any suitable photomultiplier tube to measure emitted light or spectral reading instrument may be used. Other embodiments of the invention may have any suitable label on the hormone antibody and any suitable instrument for measuring the label, such as a radio isotope label and an instrument that reads the radio isotope.

The PTH standards 16–21 and controls 22–23 contain a non-lyophilized PTH in a substantially non-protein matrix with preservatives. Other embodiments of the invention may use any non-reconstituted PTH or other hormone in the diagnostic test kit 10. In preferred embodiments of the invention, the standards 16–21 and the controls 22–23 have a shelf life at 4 degrees C. of at least six months, or, more preferably at least nine months, or, even preferably at least a year, as a result of the preservatives. Prior art diagnostic kits with an extended shelf life at 4 degrees C. employed hormone standards and controls that required reconstitution, such as freeze-dried standards and controls.

In a preferred embodiment of the invention, the matrix comprises phosphate buffered saline, but other embodiments of the invention may have other solutions, both buffered and non-buffered. In a preferred embodiment of the invention, the preservatives are polyvinyl alcohol, EDTA di-sodium salt, and sodium molybdate. In a more preferred embodiment of the invention, there is less than 1% polyvinyl alcohol, less than 1% sodium molybdate, and less than 0.5% EDTA di-sodium salt dissolved in the buffer solution. In a highly preferred embodiment of the invention, there is approximately 0.5% polyvinyl alcohol, 0.7% sodium molybdate, and 0.17% EDTA di-sodium salt, dissolved in the buffer solution.

In an embodiment of the invention, a non-specific binding reducer such as a non-ionic detergent is employed. In a preferred embodiment of the invention, the non-ionic detergent is t-octylpheoxypolyethoxyethanol sold under the brand name TRITON X-100 by Sigma of St. Louis, Mo., and is added to the standards 16–21 and controls 22–23 to correct for high non-specific binding of the non-protein matrix. In a preferred embodiment of the invention, less than 1 .5%t-octylpheoxypolyethoxyethanol is added to the matrix, and in a highly preferred embodiment of the invention, 0.5%t-octylpheoxypolyethoxyethanol is added to the matrix.

In a preferred embodiment of the invention, the standards 16–21 and the controls 22–23 are made by spiking the matrix with concentrated PTH solution. In a preferred embodiment of the invention, the standards 16–21 are spiked such that the levels of PTH therein are approximately 0, 5, 15, 50, 150 and 1500 picograms/mL respectively. Other embodiments of the invention may have more or fewer standards and the standards may have other percentages of PTH. In an embodiment of the invention, the controls 22–23 have PTH levels within the range of the standards 16–21.

In a more preferred embodiment of the invention, the concentrated PTH solution is made by compounding the PTH into the solution of the matrix. In a more highly preferred embodiment of the invention, the solution comprises the phosphate buffered saline earlier described.

In another embodiment of the invention, the concentrated PTH solution required to make the standards and controls is prepared in the above matrix with preservatives and TX100 along with a very small amount of PTH free human serum. This alternative embodiment results in a relatively low percentage of protein that is required to reduce the non-specific binding to a level acceptable for this assay in order to read the low patients correctly. In a preferred embodiment of the invention, the standards and controls are spiked with the concentrated PTH solution such that the standards and controls contain 2% of human serum.

The PTH antibody coated beads 12 are polystyrene beads coated with PTH goat polyclonal antibody. In an embodiment of the invention, there are 100 beads of suitable size. Alternatively, any other suitable solid phase, as is well known in the art, coated with the PTH antibody may be used. The acridinium ester labeled PTH antibody solution 14 is chemiluminescent labeled PTH goat polyclonal antibody in a buffered protein solution. In an embodiment of the invention, 10 mLs of the solution 14 is provided in the kit 10. In the preferred embodiment of the invention, there is 50 mLs of saline wash concentrate 24.

Other materials needed to perform the test may include 12×75 mm borosilicate glass tubes, a test tube rack, 100 $\mu$L and 200 $\mu$L precision pipettors, 100 $\mu$L and 500 $\mu$L repeating dispenser, a trigger set, luminometer performance controls, reference control sera, a bead dispenser capable of dispensing 6 mm beads, distilled or deionized water, a timer, a mixer, film to cover the tubes, a luminometer, a bead washer capable of washing 6 mm beads or repeating dispenser capable of delivering 2 mL, and a rotator capable of maintaining 180±10 rpm. The trigger set is composed of a trigger 1 and a trigger 2. The trigger 1 has 0.1N nitric acid and 0.325% hydrogen peroxide. The trigger 2 has 0.25N sodium hydroxide and 0.125% of a detergent, cetyltrimethylammonium chloride. The acridinium ester on the acridinium ester labeled PTH antibody solution 14 emits light under alkaline oxidation and the trigger set serves this purpose.

The assay procedure for analyzing a patient sample involves bringing the kit 10 to room temperature. All liquid components of the kit and all samples are mixed by gentle inversion. The saline wash concentrate 24 is diluted appropriately with the distilled or deionized water to have a concentration of 0.9% sodium chloride.

Continuing the assay procedure, the test tubes (not shown) are appropriately labeled. 200 $\mu$L of the standards 16–21, the controls 22–23, and the patient sample are delivered directly to the bottom of a respective test tube. 100 $\mu$L of antibody solution 14 is added to the bottom of each test tube and vortexed gently to avoid foaming. Next, one bead 12 is added to each test tube. In a preferred embodiment of the invention, the bead 12 is added with minimal splashing. In a more preferred embodiment of the invention, the test tube is tilted to enable the bead 12 to gently enter the solution in the test tube.

In a next step of the procedure, the liquid filled test tubes are incubated on the rotator (not shown) at 180±10 revolutions per minute (rpm) at room temperature for two hours. In a saline wash step of the assay, the beads are washed three times in an automated washing station, using 2 mL of working saline solution, after incubation. In an alternative embodiment of the invention, the beads may be manually washed. The manual washing step comprises aspirating the tubes, adding three mL of saline solution to the tubes, aspirating the tubes, and repeating three more times the adding and aspirating steps.

Next, each bead is counted in the luminometer using trigger solutions 1 and 2 for two seconds. In a preferred embodiment of the invention, the standards 16–21, the controls 22–23, and the patient samples are assayed in duplicate. The relative light unit read from the luminometer for the duplicate samples is averaged and used for the reduction of data and calculation of the results using techniques known in the art.

Borosilicate glass test tubes are used in a preferred embodiment of the invention due to their inherently low luminescence background and low non-specific binding characteristics.

Patient samples that are greater than the highest standard 21 are diluted with the zero standard 16 and reassayed with the result being multiplied by the dilution factor.

In a preferred embodiment of the invention, the assay should be performed on serum samples. Other embodiments of the invention may use EDTA plasma. Duplicate assays require 400 µL of serum. For a more accurate comparison with normal values, a fasting morning serum sample should be obtained. The blood sample is collected in a red-top venipuncture tube (no additives) and allowed to clot. The sample is centrifuged, preferably in a refrigerated centrifuge, and the serum is separated from the cells. The sample should be frozen immediately (−20° C. or below) or stored as outlined below.

| STORAGE CONDITION OF PATIENT'S SERUM | TIME |
| --- | --- |
| At room temperature after collection | 2 hours |
| Refrigerated at 4° C. | 8 hours |
| Frozen at −20° C. | 4 months |
| Frozen at −70° C. | 11 months |

There are other embodiments of the invention that may use the hormones stored with preservatives having an extended shelf life and the hormones were not previously freeze-dried or otherwise preserved in a manner that requires reconstitution for standards and controls. An example of such an embodiment is an immunoradiometric assay of intact PTH (IRMA of intact PTH). In an IRMA of intact PTH, the standards, controls, and samples are incubated with a tracer containing an antibody label using radio isotope iodine 125 and a solid phase, such as the above mentioned polystyrene beads coated with an PTH antibody. The incubation is performed with the materials being stationary at room temperature for 20 to 24 hours. The solid phase is washed twice with 2.0 mL of working wash solution and counted in a gamma counter for 1 minute. In an embodiment of the invention for the IRMA of intact PTH, the standards and controls have a buffered human serum matrix.

In another embodiment of the invention, an intact PTH diagnostic procedure involves delivering 150 µLs of two calibrators, two controls, samples, and 50 µLs of assay buffer and 25 µLs of acridinium ester labeled antibody solution into a cuvette strip. The strip is transported into an incubator chamber and incubated for 20 minutes at 37° C. After the initial incubation, 25 µLs of biotinylated antibody solution and 25 µLs of streptavidin coated magnetic particles are added to each well and the incubation is prolonged another 10 minutes. Then, the wells are washed, aspirated with the particles held to the bottom of each well with magnets, triggered, and read in a measuring chamber. This embodiment may have a reagent cartridge that holds all the reagents that go into the reaction such that the procedure may involve an automatic pipette machine. In this embodiment of the invention, the reagent cartridge and the calibrators/controls may be provided separately as opposed to being in the same kit.

In other embodiments of the invention, other hormones may be kept in a substantially non-protein matrix with preservatives. Still further embodiments of the invention may be kept in a substantially non-protein matrix with preservatives and a non-specific binding reducer. In other embodiments of the invention, diagnostic test kits may contain hormones kept in the substantially non-protein matrices described herein.

Although presently preferred embodiments of the present invention have been described in detail hereinabove, it should be clearly understood that many variations and/or modifications of the basic inventive concepts herein taught, which may appear to those skilled in the pertinent art, will still fall within the spirit and scope of the present invention, as defined in the appended claims.

What is claimed is:

1. A solution comprising a non-reconstituted parathyroid hormone and a preservative, wherein the solution has a useful life of at least six months, the preservative comprises a polyvinyl alcohol, EDTA and molybdate.

2. The solution of claim 1, wherein the preservative further comprises non-specific binding reducer t-octylphenoxypolyethoxyethanol (TX-100) and human serum; the EDTA and molybdate being dissolved EDTA di-sodium salt and dissolved sodium molybdate, respectively.

3. The solution of claim 1, wherein the preservative, expressed as a percentage of the solution, comprises less than 1% polyvinyl alcohol, less than 0.5% dissolved EDTA di-sodium salt, less than 1% dissolved molybdate, and further comprises less than 1.5% t-octylphenoxypolyethoxyethanol (TX-100), and less than 5% human serum.

4. The solution of claim 1, wherein the preservative, expressed as a percentage of the solution, comprises approximately 0.5% polyvinyl alcohol, approximately 0.17% dissolved EDTA di-sodium salt, and approximately 0.7% dissolved molybdate.

5. The solution of claim 1, and further comprising approximately 0.5% t-octylphenoxypolyethoxyethanol (TX-100) and 2.0% human serum as a non-specific binding reducer.

6. A diagnostic test system comprising:
   a. a plurality of standards of known percentages of a non-reconstituted parathyroid hormone in a solution comprising a preservative, wherein the standards have a useful shelf life of at least six months, the preservative comprises a polyvinyl alcohol, EDTA and molybdate;
   b. a solid phase coated with anti-hormone antibody; and
   c. a solution of labeled antibody of the hormone.

7. The system of claim 6, wherein the preservative comprises polyvinyl alcohol, a dissolved EDTA salt, and dissolved sodium molybdate.

8. The system of claim 6, wherein the preservative, expressed as a percentage of the standards, comprises less than 1% polyvinyl alcohol, less than 0.5% dissolved EDTA di-sodium salt, and less than 1% dissolved sodium molybdate.

9. The system of claim 6, wherein the preservative, expressed as a percentage of the standards, comprises approximately 0.5% polyvinyl alcohol, approximately 0.17% dissolved EDTA di-sodium salt, and approximately 0.7% dissolved sodium molybdate.

* * * * *